United States Patent [19]

Annis

[11] Patent Number: 4,503,332

[45] Date of Patent: Mar. 5, 1985

[54] GRAZING ANGLE DETECTOR ARRAY

[75] Inventor: Martin Annis, Cambridge, Mass.

[73] Assignee: American Science and Engineering, Inc., Cambridge, Mass.

[21] Appl. No.: 400,534

[22] Filed: Jul. 21, 1982

Related U.S. Application Data

[63] Continuation-in-part of Ser. No. 304,442, Sep. 21, 1981, abandoned.

[51] Int. Cl.³ .............................................. G01T 1/20
[52] U.S. Cl. .................... 250/366; 250/367; 250/368; 378/146
[58] Field of Search ............... 378/146; 250/366, 367, 250/368, 363 S

[56] References Cited

U.S. PATENT DOCUMENTS

| | | | |
|---|---|---|---|
| 2,841,715 | 7/1958 | Schultz | 250/361 R |
| 4,187,427 | 2/1980 | Cusano | 250/366 |
| 4,260,898 | 4/1981 | Annis | 378/146 |
| 4,317,037 | 2/1982 | Suzuki et al. | 250/367 |

FOREIGN PATENT DOCUMENTS 2007457  5/1979  United Kingdom ............... 250/367

Primary Examiner—Alfred E. Smith
Assistant Examiner—Carolyn E. Fields
Attorney, Agent, or Firm—Pollock, Vande Sande and Priddy

[57] ABSTRACT

A detector array for use in an X-ray or gamma-ray imaging system comprises a plurality of elongated tubular detector members which are juxtaposed in generally parallel relation to one another. Each detector includes a thin body of scintillator material which is so oriented relative to an X-ray beam of rectangular cross-section that the beam intercepts the scintillator material at a grazing angle, and the dimensions and orientation of the several scintillators are such that they intercept different portions of the X-ray beam respectively. The output signals from the several detectors are combined and processed to produce a display of an object being examined. The energy collected from the radiant source is greatly increased and is detected with nearly 100% efficiency.

20 Claims, 6 Drawing Figures

GRAZING ANGLE DETECTOR ARRAY

CROSS REFERENCE TO RELATED APPLICATION

This application is a continuation-in-part of my prior copending U.S. application Ser. No. 304,442 filed Sept. 21, 1981, now abandoned, for "Line Detector For X-Radiation".

BACKGROUND OF THE INVENTION

The present invention relates to an X-ray detector array operative to convert incident penetrating radiation, such as X-rays and gamma-rays (hereinafter referred to generically as X-rays) into light, and is more particularly concerned with an improved array of line detectors of the general type shown in my aforementioned prior copending U.S. application Ser. No. 304,442, now abandoned adapted to be employed with a flying spot X-ray system, e.g. of the type disclosed in Stein et al U.S. Pat. No. 3,780,291 (issued Dec. 18, 1973, and reissued Sept. 2, 1975 as U.S. Pat. No. Re. 28,544 for "Radiant Energy Imaging With Scanning Pencil Beam"), or with other types of X-ray systems employed for medical diagnostic purposes.

The system shown in the aforementioned Stein et al patent comprises an X-ray source the output of which is collimated by a stationary slit and a cooperating rotating disc having slits therein, to produce a pencil beam of X-rays which scans in a linear direction across an object being examined. X-rays which pass through said object are detected by an elongated detector which is oriented in the scan direction and which is operative to generate output signals representative of the X-ray opacity of the object in the line of scan. Multiple such lines are generated by translating the X-ray source/detector arrangement and/or the object being examined relative to one another in a direction transverse to the scan direction thereby to produce groups of signals which can be processed and used to achieve a two-dimensional image of the X-ray opacity of the object being examined.

My prior copending application Ser. No. 304,442, the disclosure of which is incorporated herein by reference, discloses an improved line detector which can be used in such an X-ray inspection system, and which is adapted to convert a line beam, pencil beam, or scanning pencil beam of X-rays into an electronic signal with a one-hundred-percent detection of the X-rays. The detector comprises an elongated tubular member fabricated of an X-ray transparent material having an interior surface which is reflective to optical photons, and which supports an elongated thin planar scintillator the plane of which is oriented at an acute angle to the direction of the beam whereby the path of the X-rays through the scintillator is longer than the thickness of the scintillator. Optical photons which are emitted by the scintillator are reflected by the interior surface of the tubular member to a photomultiplier tube which is disposed adjacent at least one end of the detector. This detector arrangement allows the use of an X-ray scintillating material which is an efficient absorber of X-rays, has very little optical afterglow, and/or which exhibits unique absorption characteristics for a specific energy of X-rays, but which, at the same time, may be a poor transmitter of visible light either because it is not very transparent, or because the scintillator material is in the form of a powder as in a conventional X-ray intensifier screen.

The present invention relates, inter alia, to a novel array of detectors of the general type described in said prior application Ser. No. 304,442, which achieves a number of advantages. More particularly:

a. The energy collected from the X-ray source is increased by a factor equal to the number of detector pairs employed in the array, thereby producing an increase in collection efficiency which may be used to improve the spatial resolution since data are taken simultaneously in each of the detectors, so that each detector may define a smaller pixel size;

b. Alternatively, the extra energy may be used to achieve higher density resolution by increasing the exposure;

c. Alternatively, the improved efficiency of collection may be used to decrease the time of exposure to the subject, e.g. the time of exposure can be decreased by a factor equal to the number of detector pairs which are employed in the array;

d. Since each of the detectors in the array views the entire subject, the problem of matching the detectors to one another is eliminated, i.e., in contrast to other systems suggested heretofor which utilize a row of small discrete detectors, it is not necessary in the present invention to normalize (i.e. match the response) of every detector at every signal height to avoid "lines" in the final image; and e. Since the several detectors in the array each produce an output signal representative of the entire subject, the signals from the several detectors can be combined in selected ways to provide various kinds of information regarding the X-ray opacity of the object being examined.

SUMMARY OF THE INVENTION

The foregoing advantages of the present invention are achieved by use of a novel detector array which is adapted to cooperate with a radiant energy source which, in the preferred embodiment of the present invention, produces a beam of radiant energy which is swept in a predetermined linear scan direction through an object being examined. The cross-section of the beam is substantially rectangular in configuration and has its longer cross-sectional dimension oriented transverse to the linear scan direction of the beam. The detector array is positioned to intercept radiant energy which has passed from the X-ray source through the object, and said array comprises a plurality of elongated tubular members that are disposed in juxtaposed parallel relation to one another with the axis of elongation of each of said tubular members being oriented substantially parallel to the linear scan direction.

As in the case of my prior copending application Ser. No. 304,442, identified above, each of the detectors in the array comprises an elongated tubular member, preferably having a rectangular cross-section, which is fabricated of a radiant energy transparent material and has an interior surface which is reflective to optical photons. Each of the tubular members includes a comparatively thin body of scintillator material which has an elongated rectangular planar surface extending in the direction of elongation of the tubular member and positioned to intercept radiant energy passing through the tubular member as the beam is swept in the linear scan direction. The length of each of said scintillators is at least equal to the linear extent of the beam scan; the width of the planar surface of each of said scintillators is a fraction of the longer cross-sectional dimension of the rectangular cross-sectional beam, whereby each of said planar surfaces is adapted to intercept only a portion of said beam as the beam is swept in its scan direction; and the planar surface of each of said scintillators is oriented to intercept its associated portion of the scanning beam at a grazing angle, different ones of said planar surfaces intercepting different portions of the beam respectively.

The elongated tubular members, comprising the several detectors in the array, are juxtaposed in at least one row of said tubular members which extends away from the radiant energy source, whereby the beam passes in succession through the tubular members in said row. In a preferred embodiment of the invention, the elongated tubular members are juxtaposed in a plurality of said rows which are superposed on one another, and the scintillator material associated with the several tubular members respectively comprises a pair of planar sheets of said scintillator material supported on opposite sides of an intervening optically opaque substrate, and disposed in the planar region extending between the superposed rows of tubular detector members. In this latter preferred embodiment of the invention, the detectors are so positioned relative to the X-ray beam that said beam impinges on both rows of detectors simultaneously, and passes in succession through the detectors in both rows, thereby to produce groups of signals from all of the detectors, which signals can then be added to or subtracted from one another preparatory to the generation of an image having specific kinds of information therein.

BRIEF DESCRIPTION OF THE DRAWINGS

The foregoing objects, advantages, construction and operation of the present invention will become readily apparent from the following description and accompanying drawings wherein.

DESCRIPTION OF THE PREFERRED EMBODIMENTS

Figure 1:
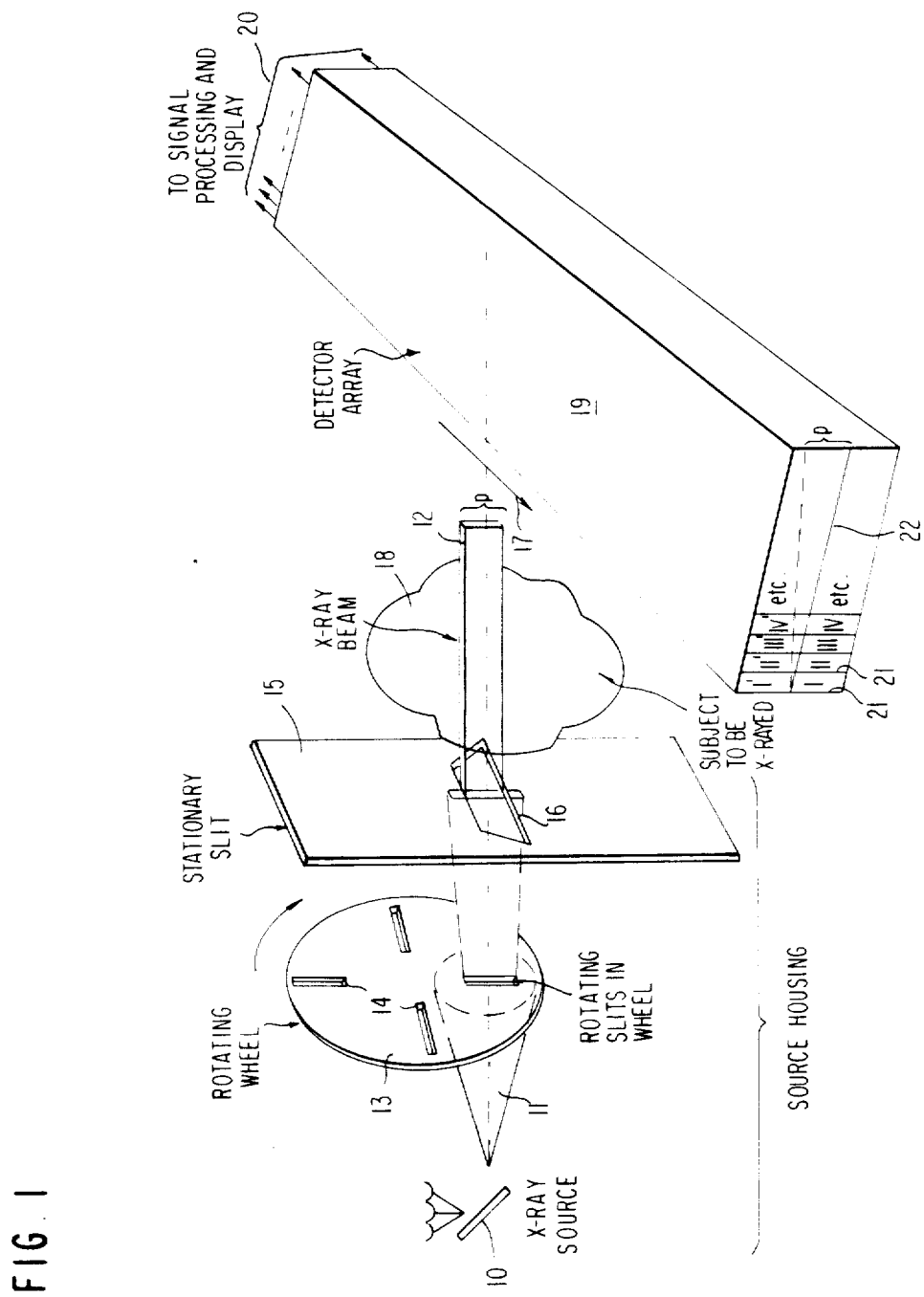
FIG. 1 is a diagrammatic perspective view of an X-ray system having a detector array constructed in accordance with the present invention.

Referring initially to FIG. 1, the X-ray system with which the detector array of the present invention is employed comprises an X-ray source 10 that produces a generally conical beam 11 of X-rays which are collimated into a flying X-ray beam 12 of rectangular cross-section by means of a rotating disk 13 fabricated of an X-ray opaque material and having a plurality of slits 14 therein, and a cooperating X-ray opaque plate 15 having a stationary slit 16 therein. The general arrangement which is used to produce the flying spot X-ray beam, and its operation, are described in the aforementioned Stein et al. U.S. Pat. No. Re 28,544; but in contrast to the arrangement shown in said prior patent, the height of stationary slit 16 is such that the X-ray beam 12 emerging therefrom has a rectangular cross-section with its longer dimension p oriented transverse to the linear scan direction of the beam, and the opposing ends of the stationary slit 16 are inclined to give the slit 16 a trapazoidal configuration, thereby to assure that the cross-sectional shape of the beam 12 remains substantially constant as each slit 14 passes from one end to the other of stationary slit 16 during rotation of wheel 13.

As each slit 14 passes from one end to the other of stationary slit 16, X-ray beam 12 scans in a generally linear direction, designated by arrow 17, through an object or subject 18 to be examined. As object 18 is scanned repetitively in direction 17, the subject 18 (or the X-ray source/collimator/detector array) is translated in a direction at right angles to scan direction 17, to effect a raster-type scanning of the subject 18 into two dimensions. The scanning beam impinges on a detector array which is generally designated 19, and which operates to produce output signals from each of the several detectors in the array at plural output points generally designated 20, one such output being provided for each detector in the array, which may be combined with one another and/or otherwise processed in a manner to be discussed hereinafter to produce a visual image representative of the X-ray opacity of the object 18 being examined.

Referring now more particularly to FIGS. 1–6, like numerals of which are used to depict like parts throughout, the detector array 19 comprises a plurality of detectors I, II, III, IV, etc., each of which has a rectangular cross-section and each of which is of elongated configuration extending generally parallel to the scan direction 17. The dimensions of the several detectors are not critical, but for purposes of the explanation which will be given hereinafter, it is assumed that each detector has a depth (in the incident direction of the X-ray beam 12) of 2 cm, a height of 4 cm, and a length in the scan direction of 1.5 meters (see FIGS. 5 and 6). Each detector comprises, moreover, a hollow tubular member 21 having an interior reflective surface formed, for example, by a layer of aluminum foil, and one wall of the tubular member is bounded by a planar sheet 22 of scintillator material having a thickness, for example, of 0.1 mm (see FIG. 6). The several detectors I, II, etc. are disposed in face-to-face juxtaposed relation to one another (see FIGS. 1, 2 and 5) to provide a row of detectors which extends away from X-ray source 10 so that as beam 12 scans in direction 17 the beam incident on detector array 19 passes through the several detectors I, II, III, etc. in succession and, in doing so, impinges upon the portion of scintillator screen 22 associated with each such detector to cause the scintillator screen to emit optical photons which are reflected by the interior surface of the tubular detector member to one or more photomultiplier tubes 23 (see FIG. 3) which are disposed at one or both ends of the elongated detector or which may be coupled to the detector at other appropriate places.

In a preferred embodiment of the invention, the array 19 includes a similarly configured second row of detectors I', II', III', etc. which is superposed on the row of detectors I, II, III, etc. and which is provided with a similar sheet of scintillating material 22a (see FIG. 4) that is separated from sheet 22 by an intervening optically opaque substrate 22b which serves to support both of the scintillator screens. When such superposed rows of detectors are employed, the detectors in row I, II, III, etc. are staggered respectively from the detectors in row I', II', III', etc. inasmuch as the scintillator 22, 22a, 22b, has a finite thickness (see FIG. 2).

Figure 6:
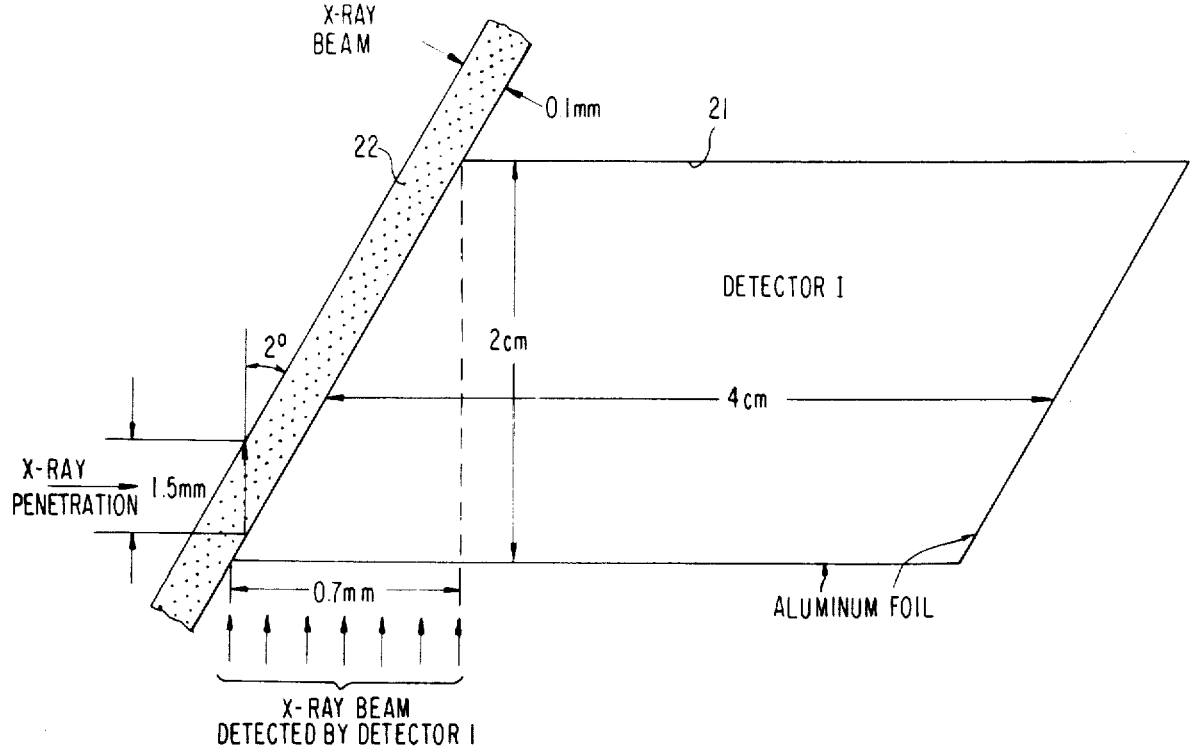
FIG. 6 is a diagrammatic cross-section of a single detector in the array of FIG. 5, showing further dimensional considerations relating to the grazing angle operation of each detector.

The overall array 19 is so oriented relative to the direction of incidence of beam 12 that said beam impinges upon the scintillator screen portion of each detector at a grazing angle $\phi$ (see FIG. 2) which, in one embodiment of the invention, may be an angle of 2° (see FIG. 6). As a result, the path of the X-rays through the scintillator is longer than the thickness of the scintillator. More particularly, referring to FIG. 6, if it be assumed that the width of each rotating slit 14 is 0.7 mm, whereby the shorter dimension of the rectangular cross-section beam 12 is 0.7 mm, then when the beam impinges upon a scintillator screen 22 having a thickness of 0.1 mm the actual X-ray penetration in screen 22 has a path length of 1.5 mm.

Due to the cross-sectional dimensions of each detector in the array, and the angular orientation of the scintillator screen associated with each detector, the projection of the angularly inclined sheet of scintillator material in a direction transverse to the scan direction 17 of the beam, is only a fraction of the longer dimension p of beam 12. The number of detectors which are employed in the rows of the array, however, are such that the projection of the complete sheet 22 in a direction transverse to the scan direction 17 of the beam has a dimension at least equal to p (see FIG. 1) whereby all portions of the beam are intercepted by the scintillator screens in the several detectors. By way of example, twenty such detectors can be employed in each row in the array each of which is adapted to intercept a 0.7 mm portion of the beam dimension p (see FIG. 6) whereby the twenty detectors collectively intercept all portions of a beam having a longer dimension p of 14 mm (see FIG. 5).

Figure 2:
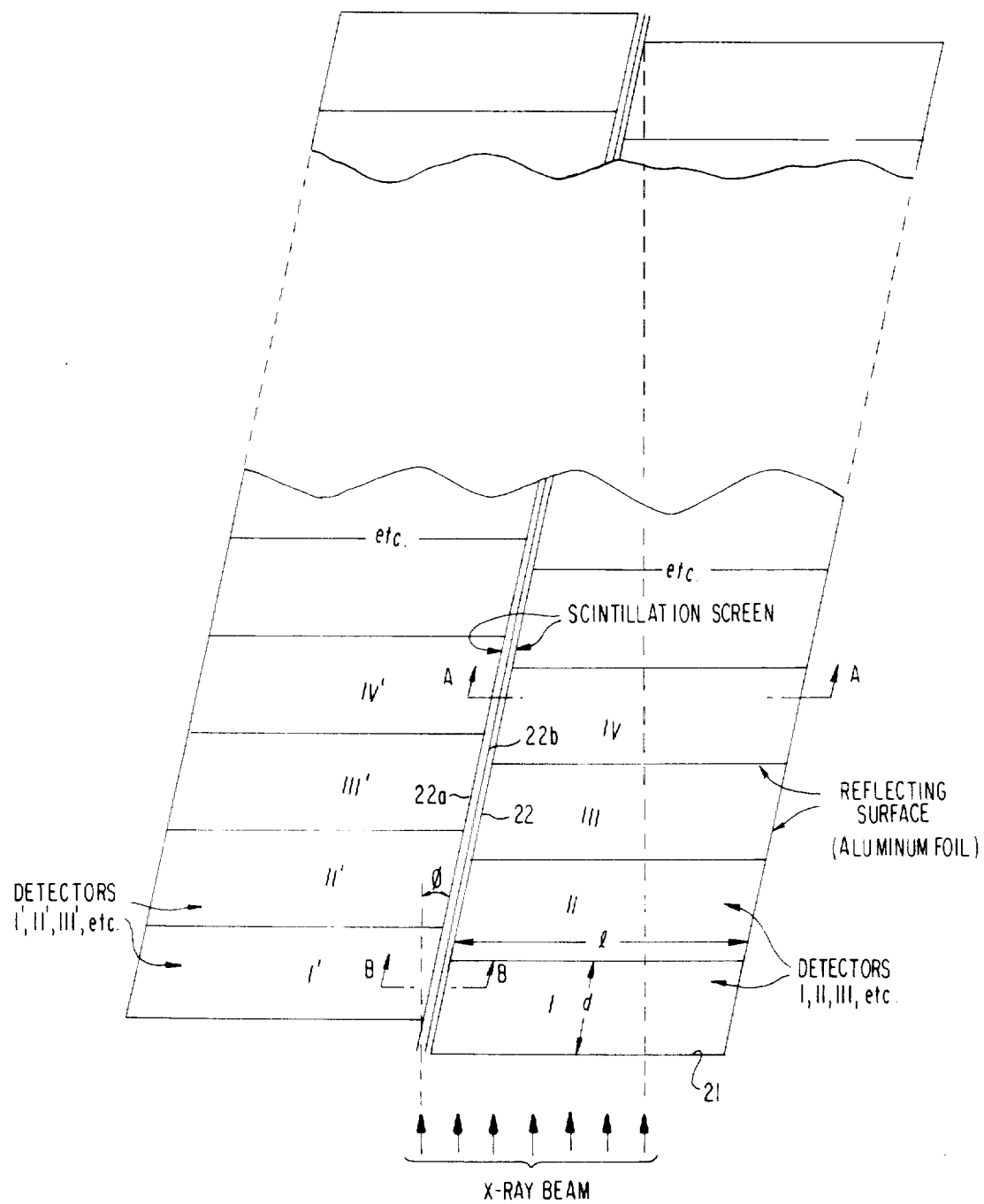
FIG. 2 is a diagrammatic cross-section of the detector array shown in FIG. 1.
Figure 3:
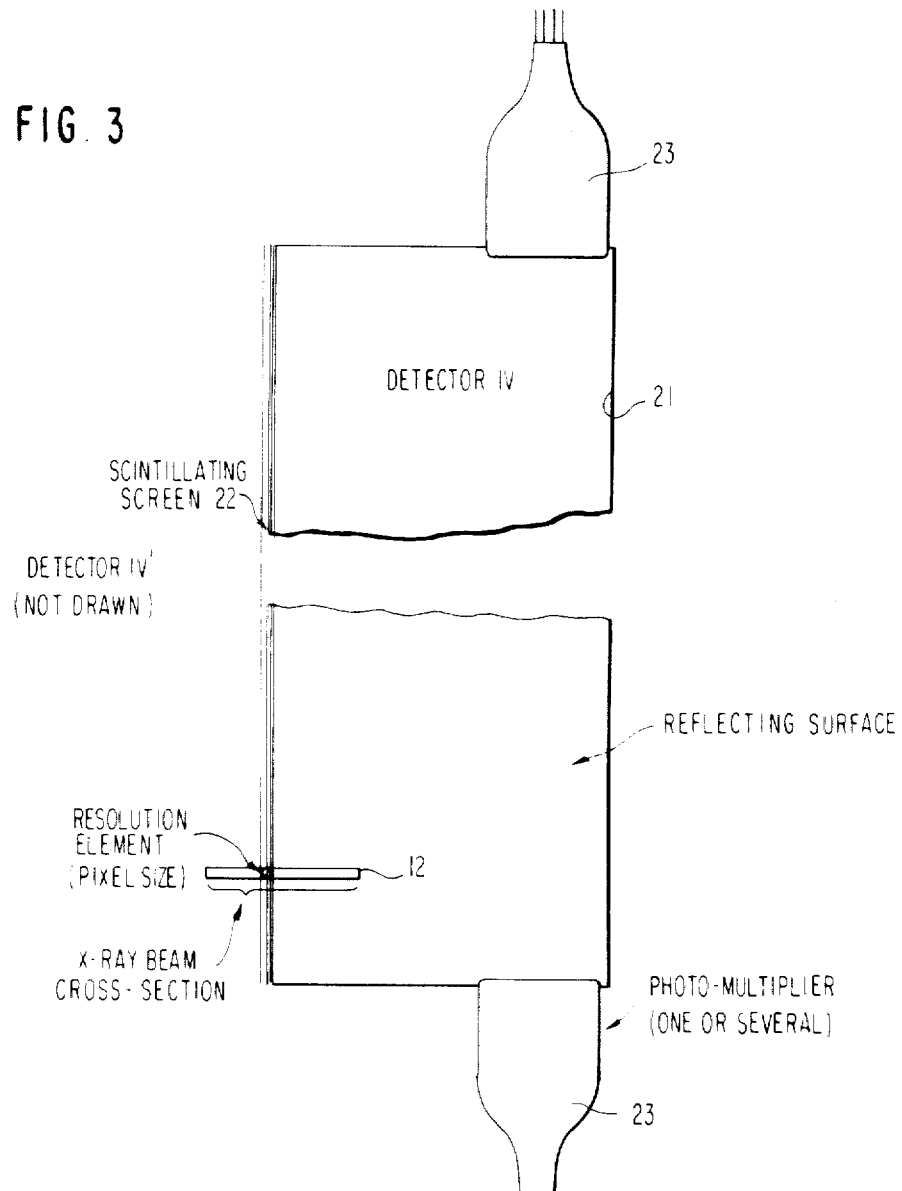
FIG. 3 is a cross-section taken on line A—A of FIG. 2.
Figure 4:
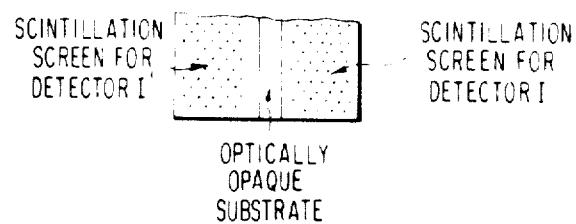
FIG. 4 is a cross-section taken on line B—B of FIG. 2.
Figure 5:
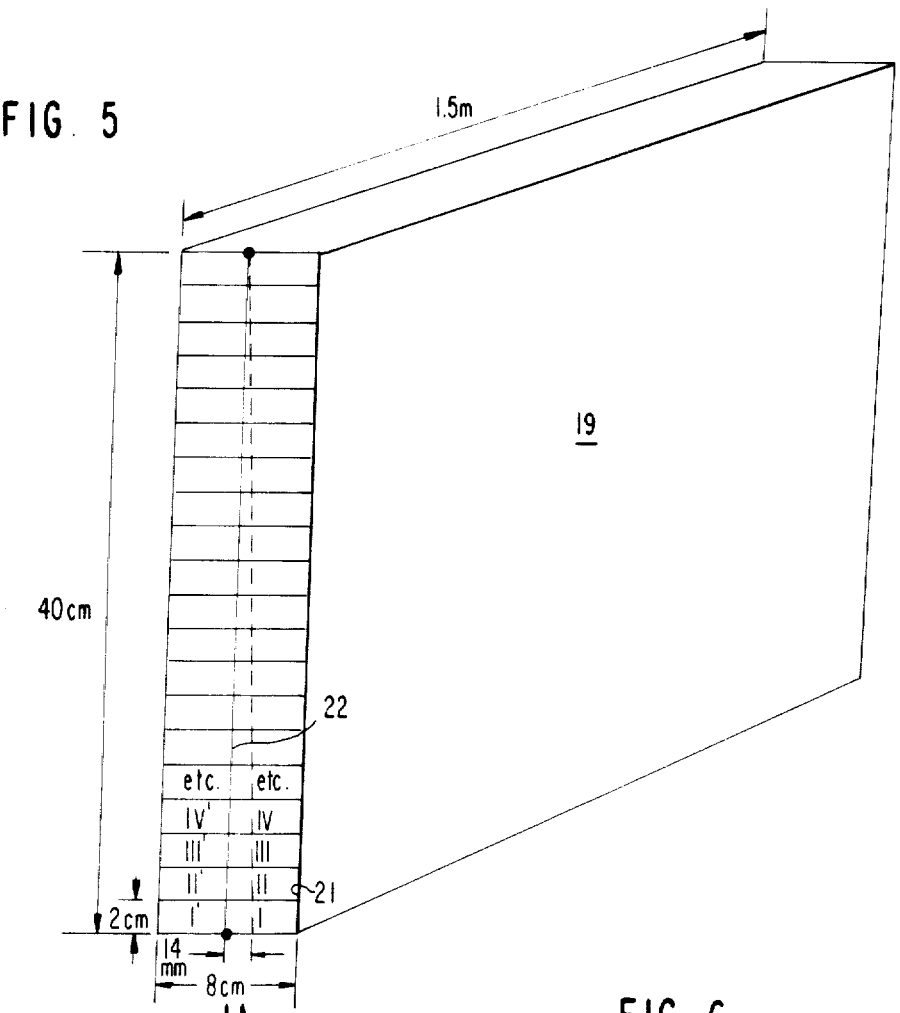
FIG. 5 is a perspective view of the detector array of the present invention, showing typical dimensions which can be employed in one embodiment of the invention.

When plural rows of detectors are employed, as shown for example in FIGS. 1, 2 and 5, the detector array is positioned relative to the beam 12 such that a line parallel to the x-ray beam and intercepting the junction of a sidewall of I, II, III, etc. and the scintillator will intercept the similar intersection in I, II, III, etc. More particularly, as noted earlier and with the dimensions shown in FIG. 6, the spatial resolution of each detector in the array is about 0.7 mm in a direction transverse to the detectors when the width of the rotating slit is made to be 0.7 mm. There is a "cross-talk" effect due to the fact that an X-ray photon incident near the upper edge of detector I', for example, (see FIG. 2) may be detected either in detector I or detector II. This effect may be made small by utilizing a thinner scintillator screen. When the scintillator screen is 0.1 mm thick, the X-ray penetration in detector I is 1.5 mm; and by employing detector pairs I, I' in parallel, the total absorption is 3 mm. The edge effect or "cross-talk" is therefore approximately 1 mm out of 7 mm, which is not unacceptably large.

In order to increase the collection efficiency, the number of detectors used in the array should be made as large as possible. As noted earlier, twenty such detectors could be used in each row of the array, i.e. twenty pairs of detectors I—I', II—II', etc. could be used; and this would result in a detector array having the dimensions shown in FIG. 5. Such an array, employing twenty pairs of detectors, would in effect be measuring twenty lines all at once; and as the relative position of the object 18 and the detector array 19 are displaced in a direction transverse to scan direction 17 between each of the several sweeps of the beam through a dimension equal to the height of each detector, the energy collected from the X-ray source is increased by a factor related to the number of detectors, or extra energy may be used to achieve a higher density resolution by increasing the dose, or the improved efficiency of collection may be used to decrease the time of exposure to the subject. By way of example in this latter respect, where twenty detectors are employed in the array, the time of exposure may be decreased by a factor of twenty thereby causing the subject to be exposed to X-rays for only a few tenths of a second.

Since each of the detectors is used to record the entire image, it is only necessary to add the signals from the several detectors together to achieve these advantages. By way of example, considering the sequence of data taken, during a first sweep of the beam a line of data would be taken with detector I. On the second sweep of the beam, another line of data would be taken with detector I, but a line of data would also be taken with detector II and added to the previous line of detector I because those two lines of data are at the same height in the object. During a third sweep of the beam, since there has been a further increment of motion of the object relative to the detector array, the first line of data from detector III would be taken from the same place in the object as the second sample from detector II, and the first sample from detector I, and all these samples would be added together; etc. This combining of the data lines is effected by an appropriate computer program or by dedicated electronic circuitry (see FIG. 1), to achieve the advantages which have been described earlier.

In combining the signals produced by the various detectors in the array, one must take into account the time delay by which each successive detector "sees" the same area of the subject delayed by a short time interval, and the combining of signals must also provide for a proper phase correction to correct for the faster sweep along successive detectors of those parts of the scanning X-ray beam corresponding to relatively greater radii along the slits in the rotating wheel 13. At or near the center of image, i.e. when the active slit 14 is perpendicular to the length of the detector array 19, no phase correction is required. Toward the edges of the image, however, the radiation encountered by successive detectors at any instant of time (i.e. for any particular data sampling interval) corresponds to projections through the subject which are successively further from the center line of the array. Before adding successive lines of data to form a final image, therefore, it is necessary to introduce a phase difference in successive lines so that the combined data samples correspond to locations in the subject that are equally distant from the center line. This phase difference may be corrected in the electronics of each detector, or alternatively may be effected by suitable software interpolation of the uncorrected measurements.

Instead of adding signals together, energy subtraction of the several signals may conveniently be done by subtracting the signal from detectors I+II+III, etc. from the signal which is produced by detectors I'+II'+III', etc. Detectors I+II+III, etc. measure the lower energy X-rays while detectors I'+II'+III' etc. measure the higher energy X-rays.

While I have thus described preferred embodiments of the present invention, many variations will be apparent to those skilled in the art. It must therefore be understood that the foregoing description is intended to be illustrative only and not limitative of the present invention, and all such variations and modifications as are in accord with the principals described are meant to fall within the scope of the appended claims.

Having thus described my invention, I claim:

1. A detector array for use with a radiant energy source that produces a beam of radiant energy which is swept in a predetermined linear scan direction through an object being examined, the cross section of said beam being substantially rectangular in configuration and having its longer cross-sectional dimension oriented transverse to said linear scan direction, said array being positioned to intercept radiant energy which has passed from said source through said object, said array comprising a plurality of elongated tubular members disposed in juxtaposed parallel relation to one another with the axis of elongation of each of said tubular members being oriented substantially parallel to said linear scan direction, each of said tubular members being fabricated of a radiant energy transparent material and having an interior surface which is reflective to optical photons, each of said tubular members including a sheet of scintillator material which has an elongated rectangular planar surface extending in the direction of elongation of said tubular member and positioned to intercept radiant energy passing through said tubular member as said beam is swept in said linear scan direction, the length of each of said planar surfaces being at least equal to the linear extent of said beam scan, the width of each of said planar surfaces being a fraction of the longer cross-sectional dimension of said beam whereby each of said surfaces intercepts only a portion of said beam as said beam is swept in said scan direction, the planar surface of each of said sheets of scintillator material being oriented to intercept said portion of said beam at a grazing angle, different ones of said planar surfaces intercepting different portions of said beam, and a plurality of light responsive elements coupled to said plurality of tubular members respectively for receiving optical photons that are emitted by said bodies of scintillator material.

2. The detector array of claim 1 wherein each of said elongated tubular members has a rectangular cross-section, the planar surface of the sheet of scintillator material associated with each of said tubular members being located adjacent an exterior flat wall of said tubular member.

3. The detector array of claim 1 wherein each of said tubular members has an elongated parallelepiped configuration, said tubular members being disposed in face-to-face relation to one another in a two dimensional array formed as a pair of superimposed rows of said tubular members, the sheets of scintillator material that are associated with said tubular members comprising portions of a substantially continuous sheet of said scintillator material which is disposed between said superimposed rows of tubular members.

4. The detector array of claim 3 wherein the tubular members in one of said rows are disposed in staggered relation to the tubular members in the other of said rows.

5. The detector array of claim 3 wherein said continuous sheet of scintillator material is disposed in a plane which is inclined at said grazing angle to the direction of incidence of said beam toward said array, the projection of said angularly inclined sheet of scintillator material having a dimension in a direction transverse to the scan direction of said beam which is substantially equal to said longer cross-sectional dimension of said beam.

6. The detector array of claim 1 wherein the planar surfaces of said sheets of scintillator material are substantially coplanar with one another.

7. The detector array of claim 1 wherein the dimensions of said elongated rectangular planar surfaces are the same for each of said tubular members whereby each of said planar surfaces intercepts a like fractional portion of said beam.

8. A radiant energy imaging apparatus comprising a radiant energy source operative to produce a beam of penetrating radiation having a rectangular cross section, scanning means for sweeping said beam in a direction transverse to the longer dimension of its rectangular cross section through an object being examined, and a detector array positioned to intercept radiant energy which has passed through said object, said detector array comprising at least one continuous sheet of scintillator material, a plurality of elongated tubular members each of which is transparent to said radiant energy and each of which includes a portion of said continuous sheet of scintillator material for emitting optical photons into said tubular member in response to radiant energy incident on the portion of said sheet that is associated with said tubular member, each of said scintillator material sheet portions having a planar surface which is oriented to intercept said incident radiant energy at a grazing angle to the direction of incidence of said beam toward the axis of elongation of the tubular member with which said sheet portion of scintillator material is associated, the positions of said plurality of tubular members relative to one another and to said source and the dimensions of the planar surfaces associated with each of said tubular members in a direction transverse to the sweep directions of said beam being such that the scintillator material sheet portions associated with different ones of said tubular members respectively intercept different portions of said beam, and a plurality of light responsive elements coupled to said plurality of tubular members for producing output signals in response to the emission of optical photons by said scintillator material sheet portions.

9. The apparatus of claim 8 wherein said elongated tubular members are juxtaposed in a row of said members which extends away from said radiant energy source, whereby said beam passes in succession through the tubular members in said row.

10. The apparatus of claim 9 wherein said elongated tubular members are juxtaposed in a pair of said rows which are superposed on one another, said beam impinging substantially simultaneously on corresponding ones of the tubular members in different ones of said rows.

11. The apparatus of claim 10 wherein said sheet of scintillator material is disposed in a plane which extends between said superposed rows.

12. The detector of claim 10 wherein the tubular members in one of said superposed rows are disposed in staggered relation to the tubular members in the other of said rows.

13. A detector for use with a radiant energy source that produces a beam of penetrating radiation which is swept in a predetermined linear scan direction, said detector comprising an elongated hollow tubular member fabricated of a material which is transparent to said radiant energy, the interior surface of said tubular member being reflective to optical photons, said tubular member being oriented in a direction parallel to said scan direction and being so positioned relative to the radiant energy source that said beam of penetrating radiation is directed toward said hollow tubular member, said hollow tubular member including an elongated sheet of scintillating material having a thickness which is a fraction of a millimeter, said sheet having a planar face positioned to intercept radiant energy passing through said tubular member, said planar face extending generally parallel to the axis of said tubular member and being oriented at a grazing angle no greater than 2° to the direction of incidence of said beam on said tubular member, and light responsive means located adjacent at least one end of said tubular member for receiving optical photons emitted by said body of scintillating material and reflected by the interior surface of said tubular member.

14. The detector of claim 13 wherein said elongated sheet of scintillating material is substantially coextensive with said elongated hollow tubular member.

15. A detector array for use with a radiant energy source that produces a beam of radiant energy which is swept in a predetermined linear scan direction through an object being examined, comprising a sheet of scintillating material disposed in a plane which is oriented at a grazing angle to the direction of incidence of said beam, a first row of elongated hollow tubular members disposed in juxtaposed relation to one another, each of the tubular members in said first row being in contact with one side of said sheet, a second row of elongated hollow tubular members disposed in juxtaposed relation to one another, each of the tubular members in said second row being in contact with the other side of said sheet, the tubular members in each of said first and second rows being oriented in directions parallel to the scan direction of said beam, each of said hollow tubular members being fabricated of a radiant energy transparent material and having an interior surface which is reflective of optical photons that are emitted by the portion of said scintillating sheet that is contacted by said tubular member when radiant energy from said source is incident on and penetrates said sheet portion, and light responsive elements coupled to said tubular members for producing output signals in response to said emitted and reflected optical photons.

16. The detector array of claim 15 wherein the thickness of said sheet is less than 1 mm.

17. The detector array of claim 15 wherein said grazing angle is in the order of 2°.

18. The detector array of claim 15 wherein said sheet comprises a pair of parallel planar scintillator screens separated from one another by an intervening optically opaque substrate.

19. The detector array of claim 15 wherein the number of tubular members in said first row is equal to the number of tubular members in said second row.

20. The detector array of claim 19 wherein each tubular member in one of said rows is disposed in staggered relation to a corresponding tubular member in the other of said rows.

* * * * *